US008003105B2

(12) United States Patent
Nakahara et al.

(10) Patent No.: US 8,003,105 B2
(45) Date of Patent: Aug. 23, 2011

(54) METHOD OF TREATING CANCER BY CO-ADMINISTRATION OF ANTICANCER AGENTS

(75) Inventors: Takahito Nakahara, Chuo-ku (JP); Kentaro Yamanaka, Chuo-ku (JP); Aya Kita, Chuo-ku (JP); Hiroshi Koutoku, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 220 days.

(21) Appl. No.: 12/493,577

(22) Filed: Jun. 29, 2009

(65) Prior Publication Data

US 2009/0263390 A1    Oct. 22, 2009

Related U.S. Application Data

(62) Division of application No. 11/965,476, filed on Dec. 27, 2007, now Pat. No. 7,618,992.

(60) Provisional application No. 60/882,809, filed on Dec. 29, 2006, provisional application No. 60/950,771, filed on Jul. 19, 2007.

(51) Int. Cl.
*A61K 39/395* (2006.01)

(52) U.S. Cl. ................ 424/155.1; 424/174.1; 424/130.1

(58) Field of Classification Search ......................... None
See application file for complete search history.

(56) References Cited

U.S. PATENT DOCUMENTS

| 6,335,194 | B1 | 1/2002 | Bennett et al. |
| 6,734,203 | B2 | 5/2004 | Matsuhisa et al. |
| 2003/0114508 | A1 | 6/2003 | Matsuhisa et al. |
| 2005/0119217 | A1 | 6/2005 | LaCasse et al. |
| 2006/0223831 | A1 | 10/2006 | Kinoyama et al. |
| 2006/0257401 | A1 | 11/2006 | Stassi et al. |

FOREIGN PATENT DOCUMENTS

| JP | 2003128548 A | 5/2003 |
| JP | 2003/521913 A | 7/2003 |

OTHER PUBLICATIONS

Nadia Zaffaroni et al., "Survivin as a target for new anticancer interventions", J. Cell. Mol. Med., 2005, 9(2):360-372.
YJ Lian et al., "Antisense RNA targeting survivin enhances the chemosensitivity of LOVO/Adr cells to taxotere", Zhonghua Wei Chang Wai Ke Za Zhi (Chinese Journal of Gastrointestinal Surgery), 2005, 8(5):455-458.
Susanne Fuessel et al., "Chemosensitization of bladder cancer cells by survivin-directed antisense oligodeoxynucleotides and siRNA", Cancer Letters, 2006, 232:243-254.
Bing Z. Carter et al., "Regulation of survivin expression through Bcr-Abl/MAPK cascade: targeting survivin overcomes imatinib resistance and increases imatinib sensitivity in imatinib-responsive CML cells", Blood, 2006, 107(4):1555-1563.
Mehdi Mesri et al., "Cancer gene therapy using a survivin mutant adenovirus", The Journal of Clinical Investigation, 2001, 108(7):981-990.
Norihiro Hayashi et al., "Adenoviral Infection of Survivin Antisense Sensitizes Prostate Cancer Cells to Etoposide In Vivo", The Prostate, 2005, 65:10-19.
Min Zhang et al., "Adenovirus-Mediated Inhibition of Survivin Expression Sensitizes Human Prostate Cancer Cells to Paclitaxel In Vitro and In Vivo", The Prostate, 2005, 64:293-302.
Takahito Nakahara et al., "YM155, a Novel Survivin Suppressant, Induced Downregulation of Survivin and Potent Antitumor Activities in Experimental Human Prostate Tumor Xenograft Models", Proceedings AACR-NCI-EORTC, 2005, Abstract No. B203.
Takahito Nakahara et al., "Tumor regression induced by YM155, a novel, small molecule survivin suppressant, in experimental human lung tumor models", Proceedings American Association Cancer Research, 2006, vol. 47, Abstract No. 5671.
A.W. Tolcher et al., "YM155, A Novel Survivin Supressant, Demonstrates Anti-tumor Activity in Patients with Advanced Solid Tumors and Non-Hodgkin's Lymphoma", Annals of Oncology, 2006, 17(Suppl. 3): 23, Abstract No. O.403.
A.W. Tolcher et al., "A phase I study of YM155, a novel survivin suppressant, administered by 168 hour continuous infusion to patients with advanced solid tumors", Journal of Clinical Oncology, 2006, 24(18S):Abstract No. 3014.
John D. Hainsworth et al., "Paclitaxel, Carboplatin, and Extended Schedule Etoposide in the Treatment of Small Cell Lung Carcinoma", Cancer, 1996, 77(12):2458-2463.
Sergio Ricci et al., "A Randomized Study Comparing Two Different Schedules of Administration of Cisplatin in Combination with Gemcitabine in Advanced Nonsmall Cell Lung Carcinoma", Cancer, 2000, 89(8):1714-1719.
H. Hagberg et al., "Randomised phase III study of R-ICE versus R-DHAP in relapses patients with CD20 diffuse large B-cell lymphoma (DLBCL) followed by high-dose therapy and a second randomisation to maintenance treatment with rituximab or not: an update of the CORAL study", Annals of Oncology, 2006, 17(Suppl. 4):iv31-iv32.
Tarun Kewalramani et al., "Rituximad and ICE as second-line therapy before autologus stem cell transplantation for relapsed or primary refractory diffuse large B-cell lymphoma", Blood, 2004, 103(10):3684-3688.
Regis Peffault De LaTour et al., "Mobilization of peripheral blood progenitor cells after DHAP regimen with or without rituximab: A large multicenter comparative study in patients with malignant lymphoma," Leukemia & Lymphoma, 2007, 48(5):897-904.
Daniel S. O'Connor et al., "A p34$^{cdc2}$ survival checkpoint in cancer", Cancer Cell, 2002, 2(1):43-54.

(Continued)

*Primary Examiner* — Sheela J Huff
(74) *Attorney, Agent, or Firm* — Sughrue Mion, PLLC (57) ABSTRACT

The present invention relates to a method of treating cancer by co-administration of an effective amount of 1-(2-methoxyethyl)-2-methyl-4,9-dioxo-3-(pyrazin-2-ylmethyl)-4,9-dihydro-1H-naphtho[2,3-d]imidazol-3-ium bromide and an effective amount of one or more anticancer agents selected from the group consisting of carboplatin, cisplatin, paclitaxel, vinorelbine, gemcitabine, irinotecan, docetaxel, doxorubicin, dacarbazine and rituximab, or a retuximab-containing combination therapy selected from R-ICE and R-DHAP. The treatment method of the present invention is useful for the treatment for all solid tumors and lymphomas, preferably skin cancer, bladder cancer, breast cancer, uterine cancer, ovary cancer, prostate cancer, lung cancer, colon cancer, pancreas cancer, renal cancer, gastric cancer and the like. Particularly, they are expected as therapeutic agents for tumor types which show resistance against existing anticancer agents.

8 Claims, 7 Drawing Sheets

OTHER PUBLICATIONS

Takahito Nakahara et al., "YM155, a Novel Small-Molecule Survivin Suppressant, Induces Regression of Established Human Hormone-Refractory Prostate Tumor Xenografts", Cancer Res., 2007, 67(17):8014-8021.

Kazuhiko Nakagawa, "Report of Shared Scientific Research Subsidized by the Ministry of Health and Labor (for Third General Anti-Cancer Strategic Research Project)", 2006, pp. 29-30.

Tsuneo Sasaki, Igaku no ayumi (Medical Progress), 1993, 164(5):251-254.

Tadato Nakahara et al., "Article from the General Annual Academic Assembly of Nippon Cancer Association", 2006, 65;495-496.

Aya Kita et al., "Article from the General Annual Academic Assembly of Nippon Cancer Association", 2006, 65:496.

Kentaro Yamanaka et al., "Article from the General Annual Academic Assembly of Nippon Cancer Association", 2006, 65:496.

Yamamoto, T., "Fundamental Studies for Gene Therapy using Survivin as a Target", Jpn. J. Cancer Chemother., vol. 30, No. 11, pp. 1805-1808, Oct. 31, 2003.

Shoji, D., "Chemotherapy-induced anemia in lymphoma patients", Hematology & Oncology, vol. 52, No. 2, pp. 216-225, Feb. 28, 2006.

Japanese Examination Report dated Jan. 6, 2011, as issued in Japanese Patent Application No. 2008/552,180.

METHOD OF TREATING CANCER BY CO-ADMINISTRATION OF ANTICANCER AGENTS

CROSS-REFERENCE TO RELATED APPLICATION

This is a divisional of application Ser. No. 11/965,476 filed Dec. 27, 2007, now U.S. Pat. No. 7,618,992, which claims benefit of Provisional Application No. 60/882,809 filed Dec. 29, 2006, and Provisional Application No. 60/950,771 filed Jul. 19, 2007. The entire disclosures of the prior applications, U.S. patent application Ser. No. 11/965,476 and U.S. Provisional Application Nos. 60/882,809 and 60/950,771 are considered part of the disclosure and are hereby incorporated by reference.

TECHNICAL FIELD

The present invention relates to a method of treating cancer by co-administration of 1-(2-methoxyethyl)-2-methyl-4,9-dioxo-3-(pyrazin-2-ylmethyl)-4,9-dihydro-1H-naphtho[2,3-d]imidazol-3-ium bromide and one or more other anticancer agents. The present invention also relates to the use of 1-(2-methoxyethyl)-2-methyl-4,9-dioxo-3-(pyrazin-2-ylmethyl)-4,9-dihydro-1H-naphtho[2,3-d]imidazol-3-ium bromide for production of medicaments for treating cancer by administration with one or more other anticancer agents.

BACKGROUND ART

Survivin is a member of the IAP (Inhibitor of Apoptosis) family of proteins, and is highly expressed in all primary tumor types. Survivin is undetectable in most normal differentiated tissues, but is present in normal placenta, testes, and rapidly dividing cells such as CD34+ bone marrow stem cells. High expression of survivin in tumors is correlated with poor survival among patients with non-small cell lung cancer (NSCLC) [Ref. 1]. Suppression of survivin induces tumor cell death and renders the cells sensitive to normal cell cycle regulation [Ref. 2-Ref. 4]. Given its preferential expression in tumor cells, its ability to block apoptosis and regulate cancer cell proliferation, and its correlation with poor survival, survivin stands out as a putative novel target for cancer therapy. It has been reported that the down-regulation of survivin expression by the antisense or siRNA of survivin was shown to sensitize tumor cells to various anticancer drugs [Ref. 7-Ref. 13].

Fused condensed imidazolium derivatives which are expected to be candidates for anti-tumor agents having good anti-tumor activity, low toxicity and wide broad safety margins are disclosed in International Publications [Ref. 5 and Ref. 6]. Particularly, 1-(2-methoxyethyl)-2-methyl-4,9-dioxo-3-(pyrazin-2-ylmethyl)-4,9-dihydro-1H-naphtho[2,3-d]imidazol-3-ium bromide (hereinafter YM155), shown by the following formula, is a compound which is expected to be useful as an anti-tumor agent, because it has good in vivo tumor growth inhibitory activity and low toxicity.

YM155 is the first compound found to specifically suppress survivin and it has potent anti-tumor activities in experimental human hormone refractory prostate cancer (HRPC) xenograft models [Ref. 14], human NSCLC xenograft models [Ref. 15], and in patients with advanced solid tumors and non-Hodgkin's lymphoma (NHL) [Ref. 16 and Ref. 17]. YM155 showed time-dependent anti-tumor activity, and 7-day continuous infusion of YM155 induced tumor regression in the NSCLC xenograft model [Ref. 15]. YM155 caused fewer side effects, e.g., body weight decrease and hematological toxicities which are frequently observed with paclitaxel, cisplatin and doxorubicin treatment [Ref. 16 and Ref. 17].

In general, there is a limit to efficacy of chemotherapy for tumors, particularly malignant tumors, when an anticancer agent is administered alone, in view of adverse reactions, and it is quite rare to attain a sufficient anticancer effect. In a clinical practice, accordingly, a multi-drug combination therapy in which 2 or more species of drugs having different mechanisms of action are used in combination has been employed. Through combination therapy, reduction of adverse drug reaction and potentiation of the anticancer activity are intended by combination of anticancer agents having different mechanisms of action, including 1) reduction of the non-sensitive cell population, 2) prevention or delaying of occurrence of drug resistance, and 3) dispersing of toxicity by means of a combination of drugs having different toxicities. With combination therapy, however, a random combination of anticancer agents having different mechanisms of action does not necessarily yield a potentiation effect of anticancer activities. Thus, studies have been conducted to obtain a combination of anticancer agents having a much higher anticancer action.

Representative combinational drugs include, for example, cisplatin and gemcitabine as well as carboplatin and paclitaxel, which are known as standard combination therapy for lung cancer [Ref. 18 and Ref. 19]. A randomized phase III study of combination therapies, R-ICE (rituximab, ifosfamide, carboplatin and etoposide) and R-DHAP (rituximab, cisplatin, Cytarabine (ara-C) and dexamethasone) is in progress in patients with lymphoma (DLBCL) [Ref. 20, 21 and 22].

When the combinational drugs are used together, there are a lot of cases where the side effects increase as well as the anti-tumor effects. Therefore there are many difficulties in combining two or more anti-tumor agents. Especially, a combination of anticancer agents with a synergistic anticancer action resulting in marked reduction of cancer cells and further complete removal of the cancer cells, leading to a complete cure of cancer without an increase of side effects, is eagerly desired.

REFERENCES

1. Monzo M, et al., J Clin Oncol 1999; 17:2100-4.
2. Giodini A, et al., Cancer Res 2002; 62:2462-7.
3. Mesri M, et al., Am J Pathol 2001; 158:1757-65.

4. Yamamoto T, et al., Med Electron Microsc 2001; 34:207-12.
5. Pamphlets of International Publication 01/60803
6. Pamphlets of International Publication 2004/092160
7. Zhonghua Wei Chang Wai Ke Za Zhi. 2005 September; 8(5):455-8
8. Cancer Lett. 2006 Feb. 8; 232(2):243-54
9. Blood. 2006 Feb. 15; 107(4):1555-63. Epub 2005 Oct. 27
10. Int. J. Cancer: 118, 812-20 (2006)
11. J Clin Invest. 2001 October; 108(7):981-90.
12. Prostate 65, 10-19 (2005)
13. The Prostate 64:293-302 (2005)
14. Proceedings AACR-NCI-EORTC 2005, Abstract #B203.
15. Proc Amer Assoc Cancer Res 2006; 47:[Abstract #5671]
16. Annals of Oncology, 2006; 17(Suppl. 3):23, Abstract #O.403.
17. Journal of Clinical Oncoclogy, 2006:ASCO Annual Meeting Proceedings Part I. Vol. 24, No. 18S (June 20 Supplement), Abstract #3014.
18. Cancer, 1996, 77:2458-63.
19. Cancer, 2000, 89:1714-9.
20. Annals of Oncology, 2006; 17(Suppl. 4):iv31-2.
21. Blood. 2006 May 15; 103(10):3684-8. Epub 2004 Jan. 22.
22. Leukemia & Lymphoma 2007 May; 48(5):897-904.

DISCLOSURE OF THE INVENTION

The present inventors have found that a combinational use of 1-(2-methoxyethyl)-2-methyl-4,9-dioxo-3-(pyrazin-2-ylmethyl)-4,9-dihydro-1H-naphtho[2,3-d]imidazol-3-ium bromide (YM155) with an existing anticancer agent or agents, particularly, docetaxel or rituximab, unexpectedly potentiates the anticancer effect. Thus, the present invention was completed.

That is, the present invention relates to a method for treatment of a cancer patient, which comprises administering an effective amount of 1-(2-methoxyethyl)-2-methyl-4,9-dioxo-3-(pyrazin-2-ylmethyl)-4,9-dihydro-1H-naphtho[2,3-d]imidazol-3-ium bromide to said patient, combined with
i) an effective amount of one or more anticancer agents selected from the group consisting of carboplatin (CBDCA), cisplatin (CDDP), paclitaxel (TXL), vinorelbine (VIN), gemcitabine (GEM), irinotecan (CPT-11), docetaxel (TXT), doxorubicin (DXR), dacarbazine (DTIC) and rituximab (RTX), or
ii) a rituximab-containing combination therapy selected from R-ICE (consisting of rituximab, ifosfamide (IFM), carboplatin and etoposide (ETP)), and R-DHAP (consisting of rituximab, cytarabine (ara-C) and cisplatin as anticancer agents).

In the invention, the preferable methods are as follows:
(1) The method as described above, wherein docetaxel or paclitaxel is combined.
(2) The method as described in (1), wherein docetaxel is combined.
(3) The method as described in (2), wherein the patient has hormone-resistant prostate cancer.
(4) The method as described above, wherein the patient has lung cancer and one or more agents selected from docetaxel, paclitaxel, carboplatin, cisplatin and gemcitabine are combined.
(5) The method as described above, wherein rituximab is combined.
(6) The method as described above, wherein a combination therapy selected from R-ICE and R-DHAP is combined.
(7) The method as described in (6), wherein R-ICE is combined.
(8) The method as described in (5) or (6), wherein the patient has lymphoma.
(9) The method as described above, wherein 1-(2-methoxyethyl)-2-methyl-4,9-dioxo-3-(pyrazin-2-ylmethyl)-4,9-dihydro-1H-naphtho[2,3-d]imidazol-3-ium bromide is administered intravenously by infusion at a dose of 1-10 mg/m$^2$/day continuously for a period of 4-14 days.
(10) The method described in (9), wherein 1-(2-methoxyethyl)-2-methyl-4,9-dioxo-3-(pyrazin-2-ylmethyl)-4,9-dihydro-1H-naphtho[2,3-d]imidazol-3-ium bromide is administered intravenously by infusion at a dose of 3-8 mg/m$^2$/day continuously for 7 days, followed by drug holidays of 14 days, which administration cycle as one cycle is repeated depending on the conditions.

The present invention also relates to the following inventions:
(11) Use of 1-(2-methoxyethyl)-2-methyl-4,9-dioxo-3-(pyrazin-2-ylmethyl)-4,9-dihydro-1H-naphtho[2,3-d]imidazol-3-ium bromide for production of a medicament for treating cancer, which is characterized by combinational administration with
i) one or more anticancer agents selected from the group consisting of carboplatin, cisplatin, paclitaxel, vinorelbine, gemcitabine, irinotecan, docetaxel, doxorubicin, dacarbazine and rituximab, or
ii) a combination therapy selected from R-ICE and R-DHAP.
(12) An agent for cancer treatment comprising as an active ingredient 1-(2-methoxyethyl)-2-methyl-4,9-dioxo-3-(pyrazin-2-ylmethyl)-4,9-dihydro-1H-naphtho[2,3-d]imidazol-3-ium bromide, which is characterized by combinational administration with
i) one or more anticancer agents selected from the group consisting of carboplatin, cisplatin, paclitaxel, vinorelbine, gemcitabine, irinotecan, docetaxel, doxorubicin, dacarbazine and rituximab, or
ii) a combination therapy selected from R-ICE and R-DHAP.
(13) A potentiator of an anticancer effect of i) one or more anticancer agents selected from the group consisting of carboplatin, cisplatin, paclitaxel, vinorelbine, gemcitabine, irinotecan, docetaxel, doxorubicin, dacarbazine and rituximab, or ii) a combination therapy selected from R-ICE and R-DHAP, which comprises as an active ingredient 1-(2-methoxyethyl)-2-methyl-4,9-dioxo-3-(pyrazin-2-ylmethyl)-4,9-dihydro-1H-naphtho[2,3-d]imidazol-3-ium bromide.
(14) A kit comprising at least one cycle dosage of 1-(2-methoxyethyl)-2-methyl-4,9-dioxo-3-(pyrazin-2-ylmethyl)-4,9-dihydro-1H-naphtho[2,3-d]imidazol-3-ium bromide and i) one or more anticancer agents selected from the group consisting of carboplatin, cisplatin, paclitaxel, vinorelbine, gemcitabine, irinotecan, docetaxel, doxorubicin, dacarbazine and rituximab, or ii) anticancer agents for a combination therapy selected from R-ICE and R-DHAP. Usually, R-DHAP contains dexamethasone as an agent for treatment of chemotherapy-induced nausea and vomiting in addition to the above-mentioned anti-cancer drugs.

BEST MODE FOR CARRYING OUT OF THE INVENTION

The following describes the invention in detail.

YM155 used in the invention is readily available according to the processes of production as disclosed in International Publication 01/60803 and International Publication 2004/092160.

YM155 may be administered orally or parenterally, and preferably intravenously. In this connection, the injection preparation for intravenous administration includes those containing sterile aqueous or non-aqueous solutions, suspensions, and emulsions. The aqueous solvent includes, for example, distilled water for injection and physiological saline. The non-aqueous solvent includes, for example, propylene glycol, polyethylene glycol, vegetable oils such as olive oil, alcohols such as ethanol, polysorbate 80 (trade name), and the like. Such compositions may contain further tonicity adjusting agents, antiseptics, moistening agents, emulsifying agents, dispersing agents, stabilizers, and solubilizing agents. These may be sterilized, for example, by filtration through a bacterial filter, blending of sterilizers or irradiation. Alternatively, it is possible to prepare a germ-free solid composition and dissolve or suspend it in sterile water or a sterile solvent for injection immediately before use.

In intravenous administration, YM155 may be administered usually at 0.1-20 mg/m²/day, preferably at 1-10 mg/m²/day, once a day or divided in plural doses, or continuously by infusion (continuous instillation). Preferably, it may be infused at 3-10 mg/m²/day continuously for a period of 4 days to 20 days, more preferably 4 days to 14 days, or 5 days, 7 days, 10 days or 14 days, and yet more preferably infused continuously for 7 days. When the administration is further continued, it is preferable to employ a medication cycle comprising a term of drug holidays of 1 day to 2 months, preferably 7 days to 21 days, more preferably 14 days, after termination of the above term of medication. In a particularly preferred embodiment, it may be administered continuously by infusion at a dose of 3-8 mg/m²/day for 7 days, followed by drug holidays of 14 days; this cycle as one cycle is repeated depending on the conditions. When an anticancer agent used in combination has a particular medication cycle, it is preferable to establish a medication cycle for YM155 and said anticancer agent so that potentiation is attained. Specifically, the frequency of administration, dosage, time of infusion, medication cycle, and the like, may be determined properly according to individual cases considering the kind of anticancer agent, state of the patients, age, gender, etc.

The following table lists existing anticancer agents suitable for combinational use with YM155 of the invention, together with the main indications of cancer. The cancers indicated for these anticancer agents in the combination therapy of the invention is not limited to these cancers.

TABLE 1

| Anticancer Agent | | Main Indications of Cancer |
| --- | --- | --- |
| Carboplatin | CBDCA | colon cancer, lung cancer |
| Cisplatin | CDDP | colon cancer, lung cancer |
| Paclitaxel | TXL | lung cancer, ovary cancer |
| Vinorelbine | VNR | lung cancer |
| Gemcitabine | GEM | lung cancer, pancreas cancer, colon cancer |
| Irinotecan | CPT-11 | colon cancer |
| Docetaxel | TXT | prostate cancer, lung cancer |
| Doxorubicin | DXR | bladder cancer |
| Dacarbazine | DTIC | malignant melanoma |
| Rituximab | RTX | CD20-positive B-cell non-Hodgkin's lymphoma |
| Ifosfamide | IFM | Third line chemotherapy of germ cell testicular cancer when used in combination with certain other approved antineoplastic agents |
| Etoposide | ETP | In combination with other approved chemotherapeutic agents as first line treatment in patients with small cell lung cancer. |
| Cytarabine | ara-C | Leukemia |

The above-mentioned anticancer agents have already been used clinically, and their administration route, administration cycle, and dose are apparent for a person skilled in the art. The appropriate dosage and administration are different depending on the species of cancer, condition and combinational agents. Detailed information is available from a variety of databases provided by the FDA, for example, "Approved Oncology Drugs" (http://www.fda.gov/cder/cancer/approved.htm)"Orange Book" (http://www.fda.gov/cder/orange/default.htm), or from the information on the home pages provided by Pharmaceuticals and Medical Devices Agency of Japan (http://www.info.pmda.go.jp/). The information about the anticancer agents stored in these databases is incorporated by reference herein in the present invention.

For example, according to the home pages provided by Pharmaceuticals and Medical Devices Agency of Japan, the package insert of TAXOTERE injection (registered trade mark; trade name of docetaxel) describes the dosage and administration of docetaxel as follows: "1. breast cancer, non-small cell lung cancer, gastric cancer, head and neck cancer; dosage and administration for each indication; 1. usually, intravenously injected by infusion at a dose of 60 mg/m² as docetaxel for an adult over 1 hour once a day at intervals of 3-4 weeks. The dosage may be increased or decreased depending on the condition, but the highest dose is up to 70 mg/m² at a time." And the package insert of RITUXAN Injection (registered trade mark; trade name of rituximab) describes as follows: "the dosage and administration: CD20-positive B-cell non-Hodgkin's lymphoma; dosage and administration 1. the recommended dosage for an adult of rituximab (genetical recombination) (JAN) is 375 mg/m² per one dose, given as an IV infusion once weekly. The maximum administering frequency is assumed to be eight times."

The following is partially extracted Dosage and Administration regarding each anticancer agent disclosed in "Approved Oncology Drugs". For practical administration, it will be appreciated naturally that the complete information has to be taken into consideration.

Docetaxel: "Breast Cancer: The recommended dose of TAXOTERE is 60-100 mg/m² administered intravenously over 1 hour every 3 weeks. Non Small Cell Lung Cancer: The recommended dose of TAXOTERE is 75 mg/m² administered intravenously over 1 hour every 3 weeks."

Carboplatin: "Single agent therapy: PARAPLATIN (trade name of carboplatin), as a single agent, has been shown to be effective in patients with recurrent ovarian carcinoma at a dosage of 360 mg/m² I.V. on day 1 every 4 weeks."

Cisplatin: "Advanced Bladder Cancer: PLATINOL-AQ (trade name of cisplatin injection) should be administered as a single agent at a dose of 50-70 mg/m² I.V. per cycle once every 3 to 4 weeks depending on the extent of prior exposure to radiation therapy and/or prior chemotherapy."

Paclitaxel: "In patients previously treated with chemotherapy for ovarian cancer, the recommended regimen is TAXOL (trade name of paclitaxel) 135 mg/m² or 175 mg/m² administered intravenously over 3 hours every 3 weeks. For patients with carcinoma of the breast, TAXOL at a dose of 175 mg/m² administered intravenously over 3 hours every 3 weeks has been shown to be effective after failure of chemotherapy for metastatic disease or relapse within 6 months of adjuvant chemotherapy."

Vinorelbine: "The usual initial dose of NAVELBINE (trade name of vinorelbine) is 30 mg/m² administered weekly. The recommended method of administration is an intravenous injection over 6 to 10 minutes."

Gemcitabine: "GEMZAR (trade name of gemcitabine) is for intravenous use only. Adults Single-Agent Use: Pancreatic Cancer—should be administered by intravenous infusion at a dose of 1000 mg/m² over 30 minutes once weekly for up to 7 weeks (or until toxicity necessitates reducing or holding a dose), followed by a week of rest from treatment. Subsequent cycles should consist of infusions once weekly for 3 consecutive weeks out of every 4 weeks."

Irinotecan: "Starting Dose and Dose Modifications Weekly Dosage Schedule: The usual recommended starting dose of CAMPTOSAR Injection (trade name of Irinotecan injection) is 125 mg/m². In patients with a combined history of prior pelvic/abdominal irradiation and modestly elevated serum total bilirubin levels (1.0 to 2.0 mg/dL) prior to treatment with CAMPTOSAR, there may be a substantially increased likelihood of grade 3 or 4 neutropenia. All doses should be administered as an intravenous infusion over 90 minutes. The recommended treatment regimen (one treatment course) is once weekly treatment for 4 weeks, followed by a 2-week rest period."

Doxorubicin: "Ovarian Cancer Patients Doxil (trade name of doxorubicin HCl liposome injection) should be administered intravenously at a dose of 50 mg/m² (doxorubicin HCl equivalent) at an initial rate of 1 mg/min to minimize the risk of infusion reactions. If no infusion-related AEs are observed, the rate of infusion can be increased to complete administration of the drug over one hour. The patient should be dosed once every 4 weeks, for as long as the patient does not progress, shows no evidence of cardiotoxicity, and continues to tolerate treatment. A minimum of 4 courses is recommended because median time to response in clinical trials was 4 months."

Dacarbazine: "Malignant Melanoma: The recommended dosage is 2 to 4.5 mg/kg/day for 10 days. Treatment may be repeated at 4 week intervals. 2 An alternate recommended dosage is 250 mg/square meter body surface/day I.V. for 5 days. Treatment may be repeated every 3 weeks."

Rituximab: The recommended dosage of RITUXAN (trade name of rituximab) is 375 mg/m² given as an IV infusion once weekly for four doses (days 1, 8, 15, and 22).

Ifosfamide: IFEX (trade name of ifosfamide) should be administered intravenously at a dose of 1.2 g/m² per day for 5 consecutive days.

Etoposide: In small cell lung cancer, the VePesid For Injection dose in combination with other approved chemotherapeutic drugs ranges from 35 mg/m²/day for 4 days to 50 mg/m²/day for 5 days.

Cytarabine: In the induction therapy of acute non-lymphocytic leukemia, the usual cytarabine dose in combination with other anticancer drugs is 100 mg/m²/day by continuous IV infusion (days 1 to 7) or 100 mg/m² IV every 12 hours (days 1 to 7). Regarding R-ICE and R-DHAP, detailed information is available from references on clinical trials as follows:

R-ICE (Blood. 2006 May 15; 103(10):3684-8): Rituximab (375 mg/m2) is administered on day 1 of each cycle and 48 hours before the initiation of the first cycle of ICE. ICE chemotherapy is administered on an inpatient basis beginning on day 3 of each cycle. Etoposide (100 mg/m²) is administered as an intravenous bolus daily for 3 days, from days 3 to 5. Carboplatin capped at 800 mg is administered as a bolus infusion on day 4. Ifosfamide (5000 mg/m²), mixed with an equal amount of mesna, was administered as a continuous intravenous infusion over 24 hours beginning on day 4. R-DHAP (Blood. 1988 January; 71:117-22, Leukemia & Lymphoma 2007 May; 48(5):897-904): Rituximab (375 mg/m²) is administered on day 1 of each cycle and 48 hours before the initiation of the first cycle of DHAP. Cisplatin (100 mg) is administered as a continuous intravenous infusion over 24 hours beginning on day 1. Cytarabine (2000 mg/m²) is administered as an intravenous bolus twice daily on day 2. Additionally, in order to control chemotherapy-induced nausea and vomiting, dexamethasone (40 mg/m²) is administered as an intravenous bolus daily for 3 days, from days 1 to 4.

In using the combination therapy of the present invention, the same dose as that usually given as a single agent or a slightly reduced dose (for example, 0.10-0.99 times the highest dose as a single agent) may be given through a normal administration route.

In the case of an anticancer agent which is administered in a certain administration cycle, the cycle may properly be adjusted so as to be suitable for combinational use with YM155. Specifically, the frequency of administration, dosage, time of infusion, medication cycle, and the like may be determined properly according to individual cases considering the state of patients, age, gender, etc.

The mode of medication in combinational administration of YM155 and an anticancer agent is not particularly limited as long as a suitable administration route, frequency of administration and dosage are properly selected. For example, (1) administration of a composition containing YM155 and an anticancer agent, i.e., as a single preparation; (2) combinational administration of 2 species of preparations separately prepared from YM155 and an anticancer agent, respectively, through the same administration route; (3) time interval difference administration of 2 species of preparations separately prepared from YM155 and an anticancer agent, respectively, through the same administration route (for example, YM155 is administered first, and then an anticancer agent, or vice versa); (4) combinational administration of 2 species of preparations separately prepared from YM155 and an anticancer agent, respectively, through different administration routes; and (5) time interval difference administration of 2 species of preparations separately prepared from YM155 and an anticancer agent, respectively, through different administration routes (for example, YM155 is administered first, and then an anticancer agent, or vice versa).

In a preferred embodiment of combinational administration of the present invention, YM155 and another anticancer agent are separately formulated, and the resulting 2 types of preparations are administered concomitantly (including partially concomitant) or at a time interval through an administration route suitable to each preparation and in a proper frequency of administration. In the time interval difference administration, it is necessary to administer the preparations at a time interval which satisfies the potentiation of the anticancer effect. Preferably, the 2nd preparation is administered within 2 weeks, more preferably 7 days, yet more preferably 3 days, after administration of the first preparation. When there is concern about a drug-drug interaction between YM155 and another anticancer agent, it is appropriate to administer them at an interval required for avoidance of such an interaction.

As shown in Test Examples, it was found that the therapeutic effect on cancer was potentiated by combination therapy of YM155 and an existing anticancer agent. The effect was confirmed by significant reduction of the tumor volume in comparison with that by the respective single application of YM155 or an existing anticancer agent. On the other hand, the body weight was equal to that at the administration of an existing anticancer agent as a single agent, indicating that possibly there is no change in adverse reaction in the combinational use. Therefore, it was found that the combinational use of YM155 and an existing anticancer agent potentiates an anticancer action with no change of adverse reaction, resulting in a satisfactory therapeutic effect for cancer.

Surprisingly, it was elucidated that a combinational use of YM155 and a taxane-type anticancer agent, particularly docetaxel, exhibited a much better cancer-regression action. In an animal model as shown in the Test Examples, an anticancer effect was confirmed which was so potent that disappearance of cancer was attained. In a combinational use with docetaxel, disappearance of cancer was observed in all or part of the animals tested, and totally the tumor volume was reduced to almost 0 (zero) after the lapse of 35 days; no tendency was observed toward the growth of cancer cells again. From this finding, it was estimated that the inhibitory effect of YM155 on expression of survivin and the anticancer effect of docetaxel worked synergistically to attain a particularly excellent therapeutic effect for cancer.

In a preliminary test using an animal model to which an other type of cancer was transplanted, e.g., prostate cancer (PC-3), a taxane-type anticancer agent, docetaxel or paclitaxel, was administered combined with YM155. As a result, the anticancer action was potentiated in comparison with administration of the respective single agents and the tumor volume was reduced well. This suggests that the combinational use of YM155 potentiates the anticancer action of existing anticancer agents and induces a good cancer therapeutic effect not limited by kinds of cancers. In addition, it has been disclosed in the above-cited references No. 14 to 17 that YM155 per se exhibits a potent anticancer action on a variety of cancers in which survivin is involved. These findings show that the method of the invention for treatment of cancers by co-administration of YM155 and an existing anticancer agent, in which the inhibitory effect of YM155 on expression of survivin and the anticancer effect of the existing anticancer agent work synergistically, affords a high therapeutic effect for cancers and can be applied to treatment of a variety of cancers. In particular, since YM155 has a new mechanism of action working to inhibit the expression of survivin, it is useful in the treatment of kinds of cancers which are resistant to existing anticancer agents.

The anticancer agents used in combination with YM155 include, preferably, those usually used against an objective kind of cancers, particularly those used in a standard therapy. For example, docetaxel for hormone-resistant prostate cancer, dacarbazine for melanoma, one or more agents selected from docetaxel, paclitaxel, carboplatin, cisplatin and gemcitabine for lung cancer, or R-ICE and R-DHAP for lymphoma, are included. The combinational use of YM155 in addition to these anticancer agents used in a standard therapy, is expected to potentiate the therapeutic effect for cancers in the objective kind of cancers.

EXAMPLES

The followings show the results of pharmacological tests indicating the usefulness of the combinational use of the invention.

Test Example 1

1) Test Compounds

The dose levels are expressed in terms of YM155, the cationic moiety of the drug substance. Docetaxel hydrate (Taxotere® INJECTION) was purchased from Sanofi-Aventis Pharma Ltd. (West Lavel, FRA) and used as docetaxel.

2) Preparation of Test Compounds

YM155 was dissolved in and diluted with physiological saline in order to prepare dosing solutions (concentrations calculated using the following formulation: dose×mean body weight for each group/daily release volume). These solutions were prepared immediately before the implantation of an osmotic pump (Alzet® model 1007D Micro-Osmotic Pump, DURECT Co., CA, USA) into the test subjects. The solutions were then loaded into the pump. Docetaxel was diluted with physiological saline to prepare 2 mg/mL solutions immediately before administration.

3) Cells

The human lung carcinoma cell line Calu 6 (HTB-56, Lot No. 208280) was obtained from American Type Culture Collection (VA, USA). The cells were cultured at 37° C. in a 5% $CO_2$ atmosphere in RPMI1640 medium supplemented with 10% heat-inactivated fetal bovine serum. The cells were collected with trypsin, suspended in PBS at $6 \times 10^7$ cells/mL, and then mixed with an equivalent volume of Matrigel® Basement Membrane Matrix (Becton Dickinson Co., Bedford, Mass., USA).

4) Animals

Five-week-old male nude mice (CAnN.Cg-Foxn1nu/Crl-Crlj(nu/nu)) were purchased from Charles River Laboratories Japan, Inc (Kanagawa, Japan). They were maintained on a standard diet and water throughout the experiments under specific pathogen-free conditions. The cells were cultured in vitro and $3 \times 10^6$ cells/0.1 mL/mouse were grafted subcutaneously into the flank of 6-week-old nude mice. The mice with tumor volumes (length×width$^2$×0.5) of 97.3 to 182.7 mm$^3$ were divided into groups. This was done using SAS software in order to minimize intragroup and intergroup tumor volume variation.

5) Administration and Measurement

The first day of administration was designated day 0, and observation continued until day 35. Each group (n=8) was treated as follows.

| | |
|---|---|
| Vehicle control group | Vehicle |
| YM155 group | YM155 2 mg/kg/day (7-day sc continuous infusion) |
| Docetaxel group | Docetaxel 20 mg/kg/day (iv bolus on day 0, 4, and 8) |
| Combination group | YM155 2 mg/kg/day + Docetaxel 20 mg/kg/day |

For 7-day sc continuous infusion, an osmotic pump containing either YM155 or physiological saline, was implanted in the dorsum of each animal while under anesthesia. The vehicle control group received a 7-day sc continuous infusion of physiological saline starting on day 0, and iv bolus injection of physiological saline on days 0, 4 and 8. The YM155 group received a 7-day sc continuous infusion of YM155 at 2 mg/kg/day starting on day 0, and iv bolus injection of physiological saline on days 0, 4 and 8. The docetaxel group received iv bolus injection of docetaxel at 20 mg/10 mL/kg on days 0, 4 and 8, as well as a 7-day sc continuous infusion of physiological saline starting on day 0. The combination group received both compounds instead of the vehicle, similarly to the YM155 and docetaxel groups.

Body weight and tumor diameter were measured every 3-4 days using calipers, and tumor volume was determined by calculating the volume of an ellipsoid using the formula: length×width$^2$×0.5. Antitumor activities are expressed as percent inhibition of tumor growth (% inh) and percent regression of the tumor (% reg). The percent inhibition of tumor growth on day 35 was calculated for each group using the following formula: 100×[1−{(mean tumor volume of each group on day 35)−(mean tumor volume of each group on day 0)}/{(mean tumor volume of the control group on day 35)−(mean tumor volume of the control group on day 0)}]. The percent regression of the tumor was calculated for all groups with observed tumor regression, using the following formula: 100×{1−(mean tumor volume of each group on day 35)/(mean tumor volume of each group on day 0)}. The number of Complete Regressions (CRs) in all groups were checked during the experimental period. The CR is defined by instances in which the tumor burden falls bellow the limit of palpation.

6) Statistical Analysis

Values are expressed as the mean± the standard error of the mean (SEM). Tumor volume and body weight on day 35 were compared between each single compound group and combination group using the Student's t-test. P values of less than 5% are considered significant. SAS software was used for data processing.

7) Results

Figure 1:
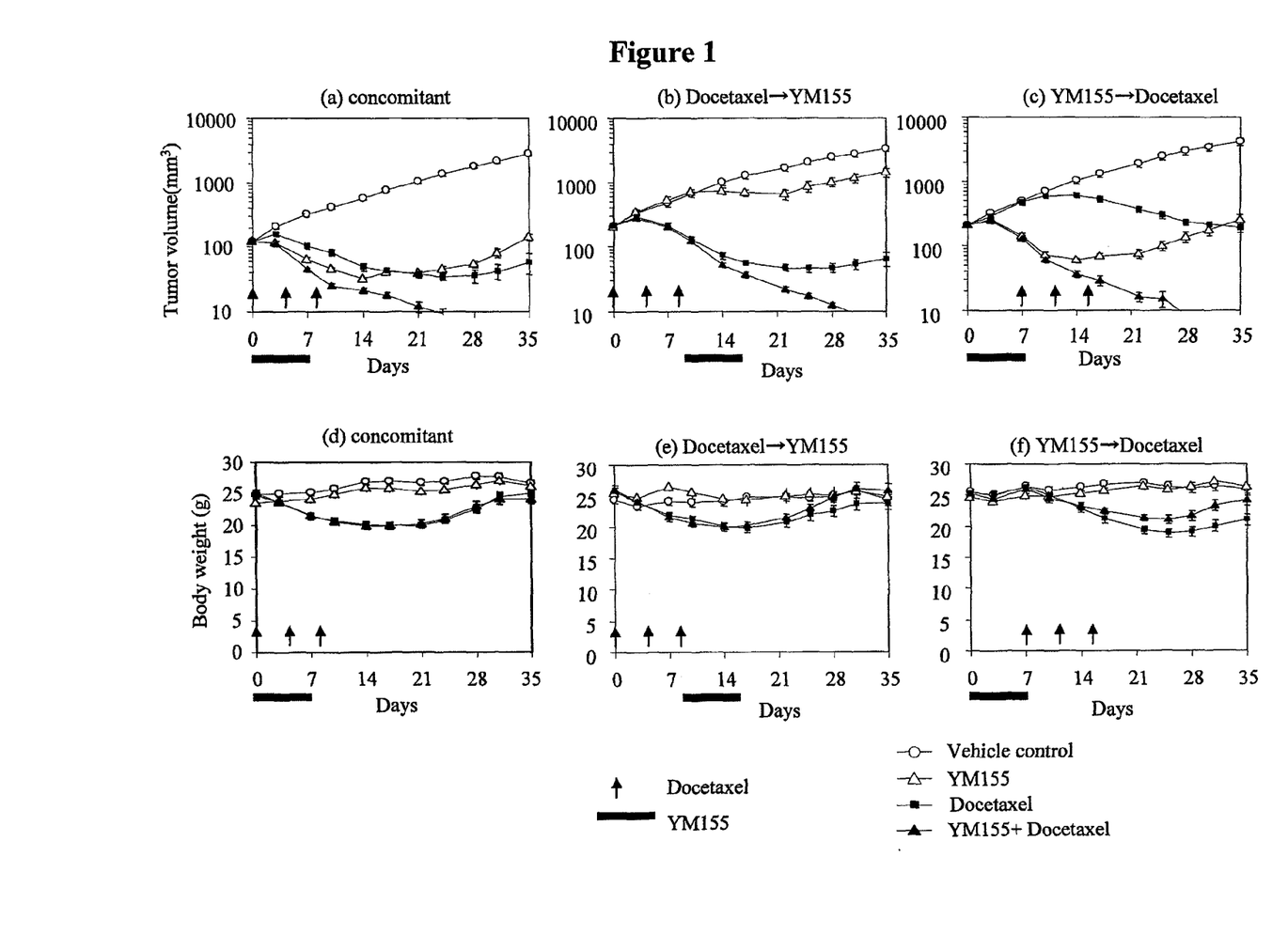
FIG. 1 contains graphs showing the results of Test Examples 1 and 2 in which YM155 was administered in combination with docetaxel. (a)-(c) are graphs respectively showing the tumor volume (mm$^3$) in Test Example 1, Test Example 2B) and Test Example 2A); (d)-(f) are graphs respectively showing body weight (g) in Test Example 1, Test Example 2B) and Test Example 2A).

When the anti-tumor activity of YM155 in combination with docetaxel was examined, the combination of YM155 at 2 mg/kg/day with docetaxel at 20 mg/kg/day completely inhibited tumor growth (>100%), and induced complete regression by 100% (Table 2 and FIG. 1-(a)). YM155 treatment alone inhibited tumor growth by 99% on day 35. Docetaxel also exhibited complete inhibition (>100%) of tumor growth, and induced tumor regression by 52% on day 35. During the 5 weeks of observation, YM155 or docetaxel treatment group showed tumor regression only during the first few weeks which was followed by successive tumor regrowth during the last few weeks. On the other hand, YM155 in combination with docetaxel showed complete regression of the tumors in all cases on day 35. No statistically significant decrease in body weight was observed in the combination group as compared to docetaxel group (FIG. 1-(d)).

TABLE 2

| Treatment Groups | Tumor Volume (mm$^3$) | | Body Weight (g) | Antitumor Activity | Number of Complete |
| --- | --- | --- | --- | --- | --- |
| | day 0 | day 35 | day 35 | (% inh/% reg) | Regressions |
| Vehicle Control | 120.9 ± 7.0 | 2848.0 ± 185.1 | 26.56 ± 0.56 | — | 0/8 |
| YM155 | 121.4 ± 6.9 | 142.3 ± 16.9 | 26.13 ± 0.56 | 99% | 0/8 |
| Docetaxel | 121.4 ± 7.0 | 58.0 ± 20.4 | 24.95 ± 0.54 | >100%/52% | 0/8 |
| YM155 + Docetaxel | 121.1 ± 7.2 | 0.0 ± 0.0$^{¶\#\#}$ | 24.11 ± 0.66$^{\#,N.S.}$ | >100%/100% | 8/8 |

Values are expressed as the mean ± SEM (n = 8).
$^¶$P < 0.05 versus Docetaxel group,
$^{\#\#}$P < 0.01 versus YM155 group,
$^\#$P < 0.05 versus YM155 group,
$^{N.S.}$no significance from Docetaxel group (Student's t-test).

8) Discussion

Results of this study indicate that YM155 significantly potentiate the anti-tumor activity of docetaxel without an increase in systemic toxicity, which is evidenced by overt symptoms such as body weight loss. The results also suggest that YM155 in combination with docetaxel is tolerated by mice, and that makes a strong combination for the treatment of cancer.

Test Example 2

The following study was conducted in the same way as Test Example 1 except for the administration timing.
A) The first day of administration was designated day 0, and observation continued until day 35. Each group (n=8) was treated as follows.

| Vehicle control group | Vehicle |
| --- | --- |
| YM155 group | YM155 2 mg/kg/day (7-day sc continuous infusion) |
| Docetaxel group | Docetaxel 20 mg/kg/day (iv bolus on day 7, 11, and 15) |
| Combination group | YM155 2 mg/kg/day → Docetaxel 20 mg/kg/day |

For 7-day sc continuous infusion, an osmotic pump containing either YM155 or physiological saline, was implanted in the dorsum of each animal while under anesthesia. The vehicle control group received a 7-day sc continuous infusion of physiological saline starting on day 0, and iv bolus injection of physiological saline on days 7, 11 and 15. The YM155 group received a 7-day sc continuous infusion of YM155 at 2 mg/kg/day starting on day 0 and iv bolus injection of physiological saline on days 7, 11 and 15. The docetaxel group received iv bolus injection of docetaxel at 20 mg/10 mL/kg on days 7, 11 and 15, as well as a 7-day sc continuous infusion of physiological saline starting on day 0. The combination group received both compounds instead of the vehicle, similarly to the YM155 and docetaxel groups.

Results

When the anti-tumor activity of YM155 in sequential combination with docetaxel was examined, the combination of YM155 at 2 mg/kg/day with docetaxel at 20 mg/kg/day completely inhibited tumor growth (>100%), and induced complete regression by 99% (Table 3 and FIG. 1-(c)). YM155 treatment alone inhibited tumor growth by 99% on day 35. Docetaxel also exhibited complete inhibition (>100%) of tumor growth, and induced tumor regression by 10% on day 35. During the 5 weeks of observation, YM155 or docetaxel treatment group showed tumor regression only during the first few weeks which was followed by successive tumor regrowth during the last few weeks. On the other hand, YM155 in combination with docetaxel showed complete regression of the tumors in all cases, and tumor volume was significantly (P<0.01) reduced in mice treated with YM155 in combination with docetaxel as compared to each single compound treatment on day 35. No statistically significant decrease in body weight was observed in the combination group as compared to Docetaxel group (FIG. 1-(f)).

group received a 7-day sc continuous infusion of YM155 at 2 mg/kg/day starting on day 8, and iv bolus injection of physiological saline on days 0, 4 and 8. The docetaxel group received iv bolus injection of docetaxel at 20 mg/10 mL/kg on days 0, 4 and 8, as well as a 7-day sc continuous infusion of physiological saline starting on day 8. The combination group received both compounds instead of the vehicle, similarly to the YM155 and docetaxel groups.

Results

When the anti-tumor activity of YM155 in sequential combination with docetaxel was examined, the combination of YM155 at 2 mg/kg/day with docetaxel at 20 mg/kg/day completely inhibited tumor growth (>100%), and induced complete regression by 97% (Table 4 and FIG. 1-(b)). YM155 treatment alone inhibited tumor growth by 61% on day 35. Docetaxel also exhibited complete inhibition (>100%) of tumor growth, and induced tumor regression by 68% on day 35. During the 5 weeks of observation, YM155 or docetaxel

TABLE 3

| Treatment Groups | Tumor Volume (mm³) | | Body Weight (g) | Antitumor Activity | |
|---|---|---|---|---|---|
| | day 0 | day 35 | day 35 | (% inh/% reg) | Number of CRs |
| Vehicle Control | 208.5 ± 18.6 | 4237.0 ± 545.7 | 25.88 ± 0.70 | — | 0/8 |
| YM155 | 208.5 ± 18.6 | 251.8 ± 50.7 | 26.25 ± 0.25 | 99%/— | 0/8 |
| Docetaxel | 209.1 ± 18.3 | 188.8 ± 29.1 | 21.03 ± 0.94 | >100%/10% | 0/8 |
| YM155→Docetaxel | 208.6 ± 18.1 | 1.3 ± 1.3¶##  | 24.13 ± 0.78¶# | >100%/99% | 7/8 |

Values are expressed as the mean ± SEM (n = 8).
¶¶p < 0.01 versus Docetaxel group,
p < 0.01 versus YM155 group,
p < 0.05 versus YM155 group,
¶p < 0.05 versus Docetaxel group (Student's t-test).

B) The first day of administration was designated day 0, and observation continued until day 35. Each group (n=8) was treated as follows.

| | |
|---|---|
| Vehicle control group | Vehicle |
| YM155 group | YM155 2 mg/kg/day (7-day sc continuous infusion) |
| Docetaxel group | Docetaxel 20 mg/kg/day (iv bolus on day 0, 4, and 8) |
| Combination group | Docetaxel 20 mg/kg/day → YM155 2 mg/kg/day |

For 7-day sc continuous infusion, an osmotic pump containing either YM155 or physiological saline, was implanted in the dorsum of each animal while under anesthesia. The vehicle control group received a 7-day sc continuous infusion of physiological saline starting on day 8, and iv bolus injection of physiological saline on days 0, 4 and 8. The YM155 treatment group showed tumor regression only during the first few weeks which was followed by successive tumor regrowth during the last few weeks. On the other hand, YM155 in combination with docetaxel showed complete regression of the tumors in three cases, and tumor volume was significantly (P<0.01) reduced in mice treated with YM155 in combination with docetaxel as compared to each single compound treatment on day 35. No statistically significant decrease in body weight was observed in the combination group as compared to docetaxel group (FIG. 1-(e)).

TABLE 4

| Treatment Groups | Tumor Volume (mm³) | | Body Weight (g) | Antitumor Activity | |
|---|---|---|---|---|---|
| | day 0 | day 35 | day 35 | (% inh/% reg) | Number of CRs |
| Vehicle Control | 207.7 ± 23.5 | 3380.8 ± 325.4 | 24.33 ± 0.85 | — | 0/8 |
| YM155 | 206.9 ± 21.8 | 1437.5 ± 225.5 | 24.80 ± 1.01 | 61%/— | 0/8 |
| Docetaxel | 210.0 ± 22.6 | 67.2 ± 15.1 | 23.84 ± 1.01 | >100%/68% | 0/8 |
| Docetaxel →YM155 | 210.1 ± 20.4 | 5.5 ± 1.7¶¶## | 25.74 ± 1.13$^{N.S.,N.S.}$ | >100%/97% | 3/8 |

Values are expressed as the mean ± SEM (n = 8).
¶¶p < 0.01 versus Docetaxel group,
p < 0.01 versus YM155 group,
$^{N.S.}$no significance from YM155 group and Docetaxel group (Student's t-test).

Test Example 3

The study was conducted in the same way as Test Example 1, except that the listed agents in Table 5 were used instead of Docetaxel according to the following dosage regimen.

TABLE 5

Figure 2:
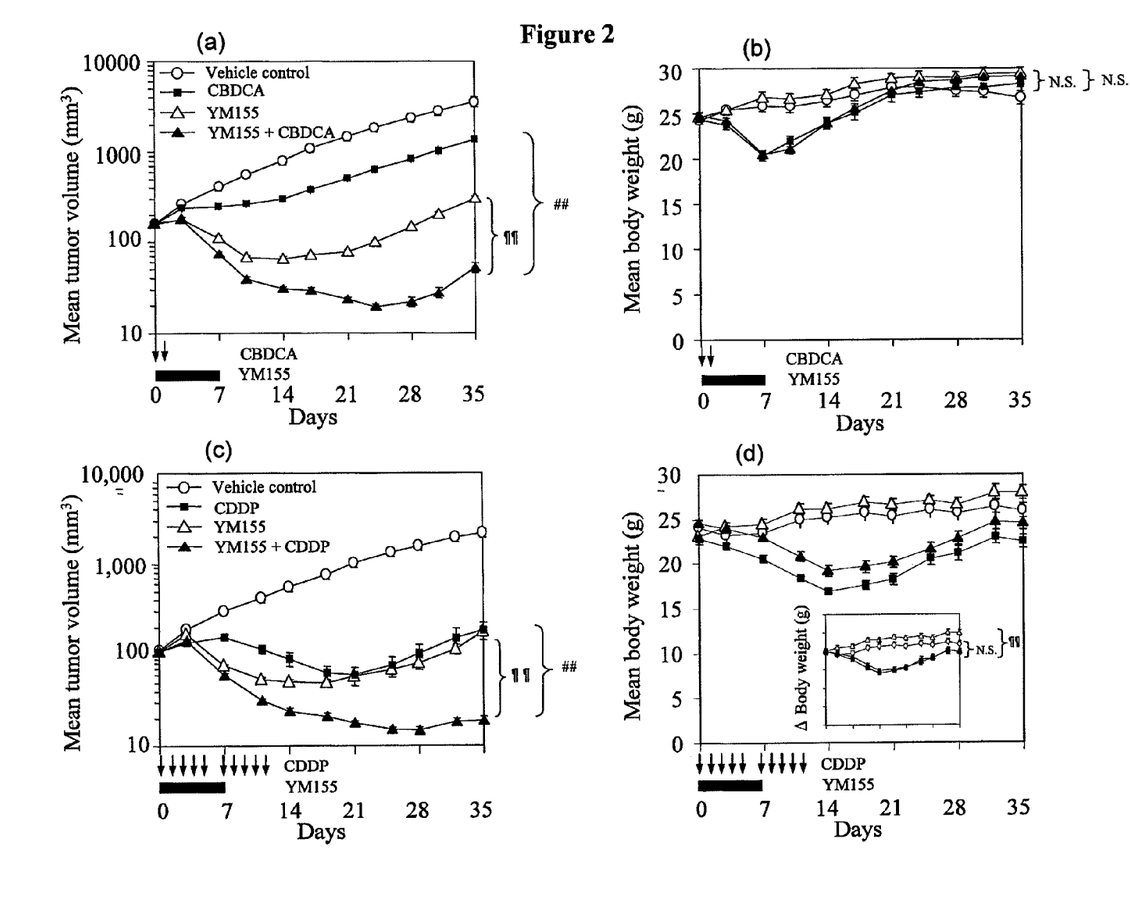
FIG. 2, (a) shows the mean tumor volume (mm$^3$) from co-administration of YM155 and carboplatin (CBDCA) in Test Example 3, and (b) shows the mean body weight (g), respectively. (c) shows the mean tumor volume (mm$^3$) from co-administration of YM155 and cisplatin (CDDP) in Test Example 3, and (d) shows the mean body weight (g), respectively.
Figure 3:
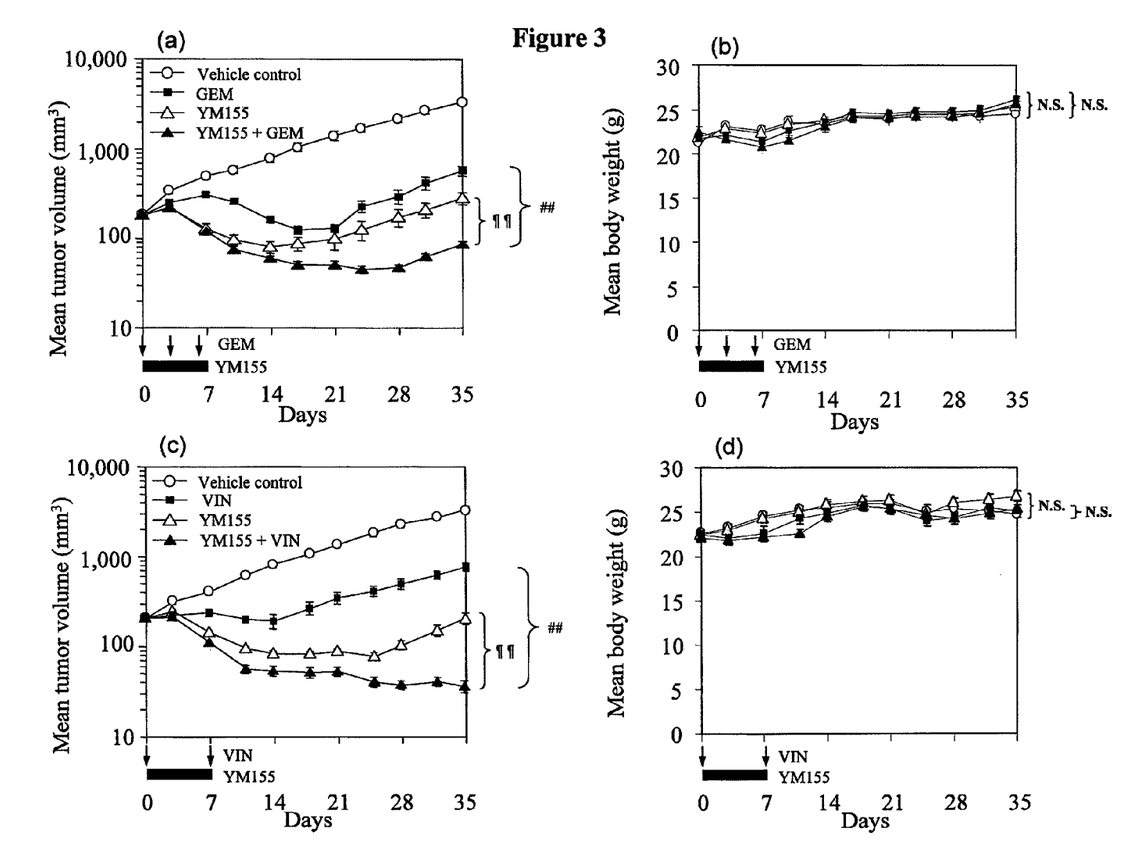
FIG. 3, (a) shows the mean tumor volume (mm$^3$) from co-administration of YM155 and gemicitabine (GEM) in Test Example 3, and (b) shows the mean body weight (g), respectively. (c) shows the mean tumor volume (mm³) from co-administration of YM155 and vinorelbine (VIN) in Test Example 3, and (d) shows the mean body weight (g), respectively.
Figure 4:
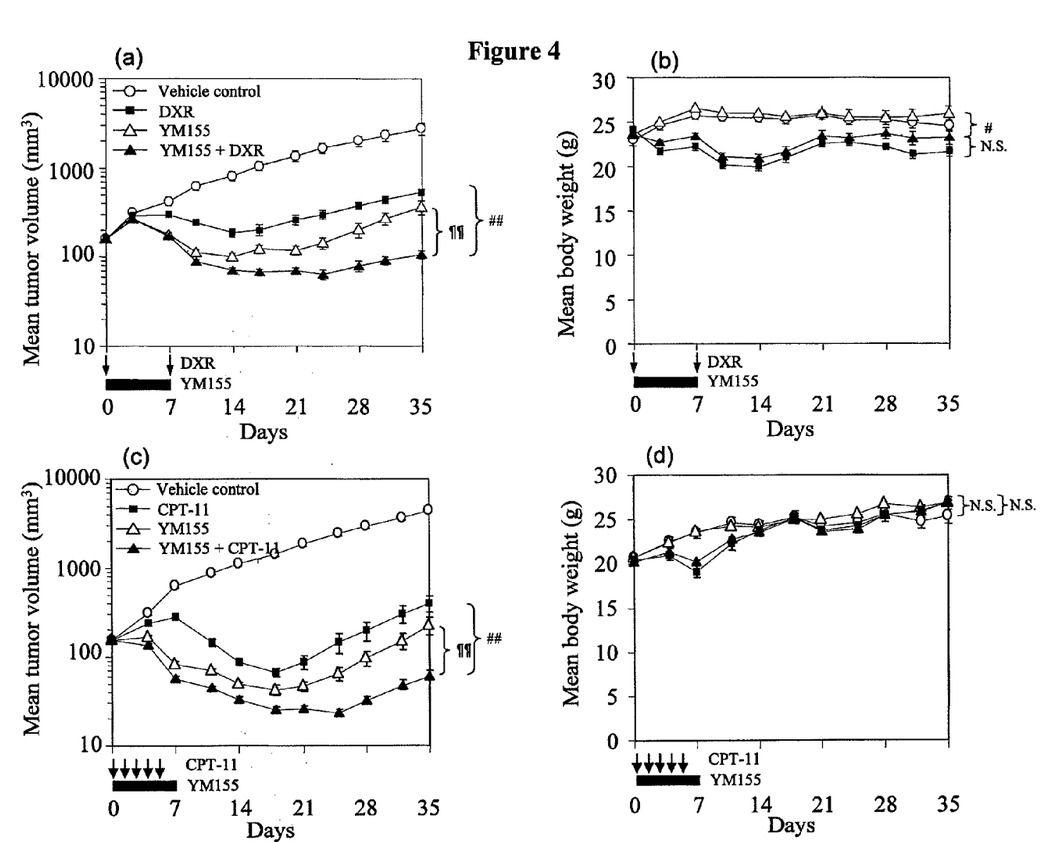
FIG. 4, (a) shows the mean tumor volume (mm³) from co-administration of YM155 and doxorubicin (DXR) in Test Example 3, and (b) shows the mean body weight (g), respectively. (c) shows the mean tumor volume (mm³) from co-administration of YM155 and irinotecan (CPT-11) in Test Example 3, and (d) shows the mean body weight (g), respectively.
Figure 5:
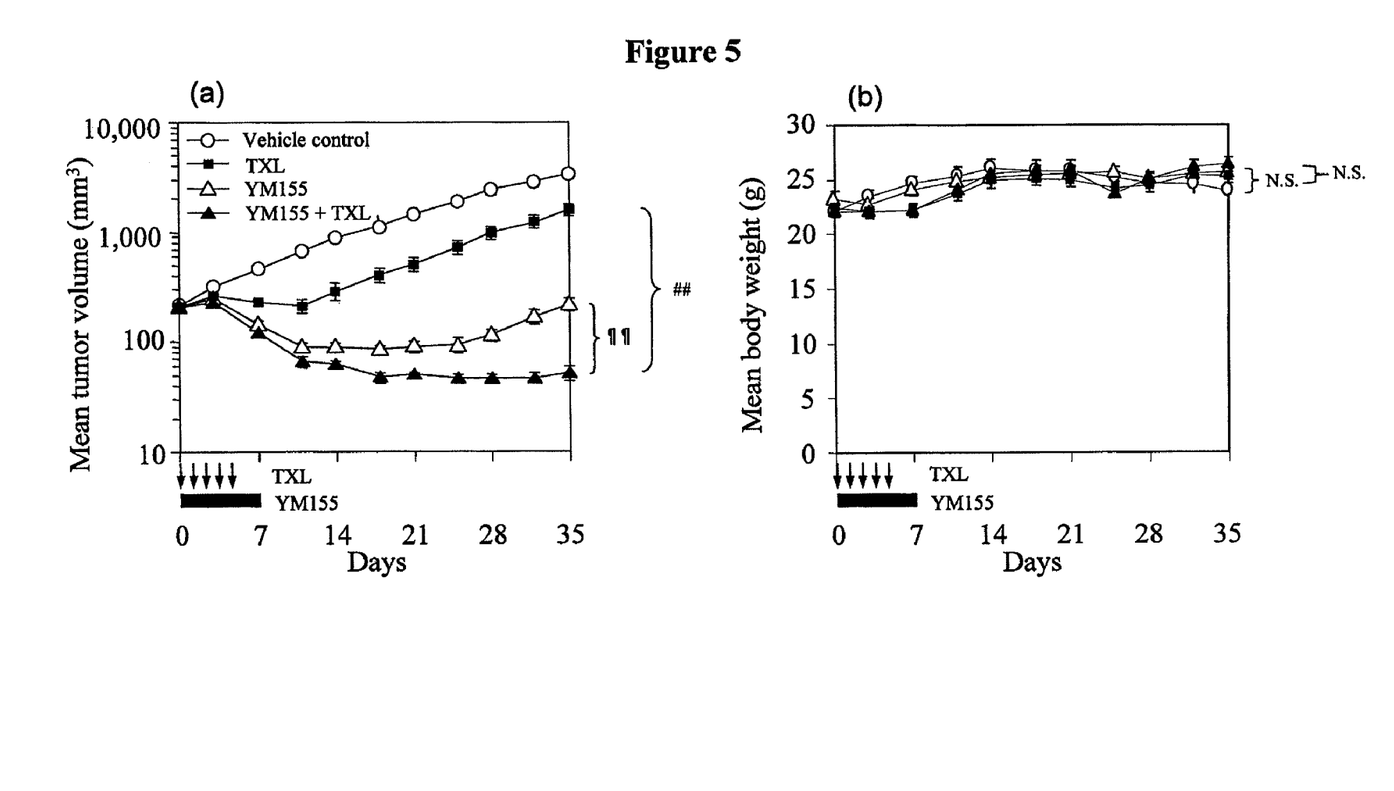
FIG. 5, (a) shows the mean tumor volume (mm³) from co-administration of YM155 and paclitaxel (TXL) in Test Example 3, and (b) shows the mean body weight (g), respectively.

| Anticancer Agent | | Dosage Regimen | Result |
|---|---|---|---|
| Carboplatin | CBDCA | 60 mg/kg/day i.v. (day 0, 1) | FIG. 2-(a) & (b) |
| Cisplatin | CDDP | 3 mg/kg/day i.v. (day 0-4, 7-11) | FIG. 2-(c) & (d) |
| Gemcitabine | GEM | 200 mg/kg/day i.v. (day 0, 3, 6) | FIG. 3-(a) & (b) |
| Vinorelbine | VNR | 10 mg/kg/day i.v. (day 0, 7) | FIG. 3-(c) & (d) |
| Doxorubicin | DXR | 10 mg/kg/day i.v. (day 0, 7) | FIG. 4-(a) & (b) |
| Irinotecan | CPT-11 | 60 mg/kg/day i.v. (day 0-4) | FIG. 4-(c) & (d) |
| Paclitaxel | TXL | 10-15 mg/kg/day i.v. (day 0-4) | FIG. 5-(a) & (b) |

(In the Table 5, i.v. means intravenous administration, for example, (day 0, 1) means once-a-day administration at the initial day of administration (day 0) and at the 1st day (day 1); (day 0-4) means once-a-day administration from the initial day of administration (day 0) to the 4th day (day 4), respectively.)

Results were shown in FIGS. 2 to 5. In the figures, values are expressed as the mean±SEM (n=8). ¶¶: P<0.01 versus an anticancer agent group, ##: P<0.01 versus YM155 group, #: P<0.05 versus YM155 group, N.S.: no significance from YM155 group and the anticancer agent group (Student's t-test).

The respective anticancer agents were purchased as commercially available products, and prepared according to the procedure directed in package inserts to use in the tests.

Test Example 4

Figure 6:
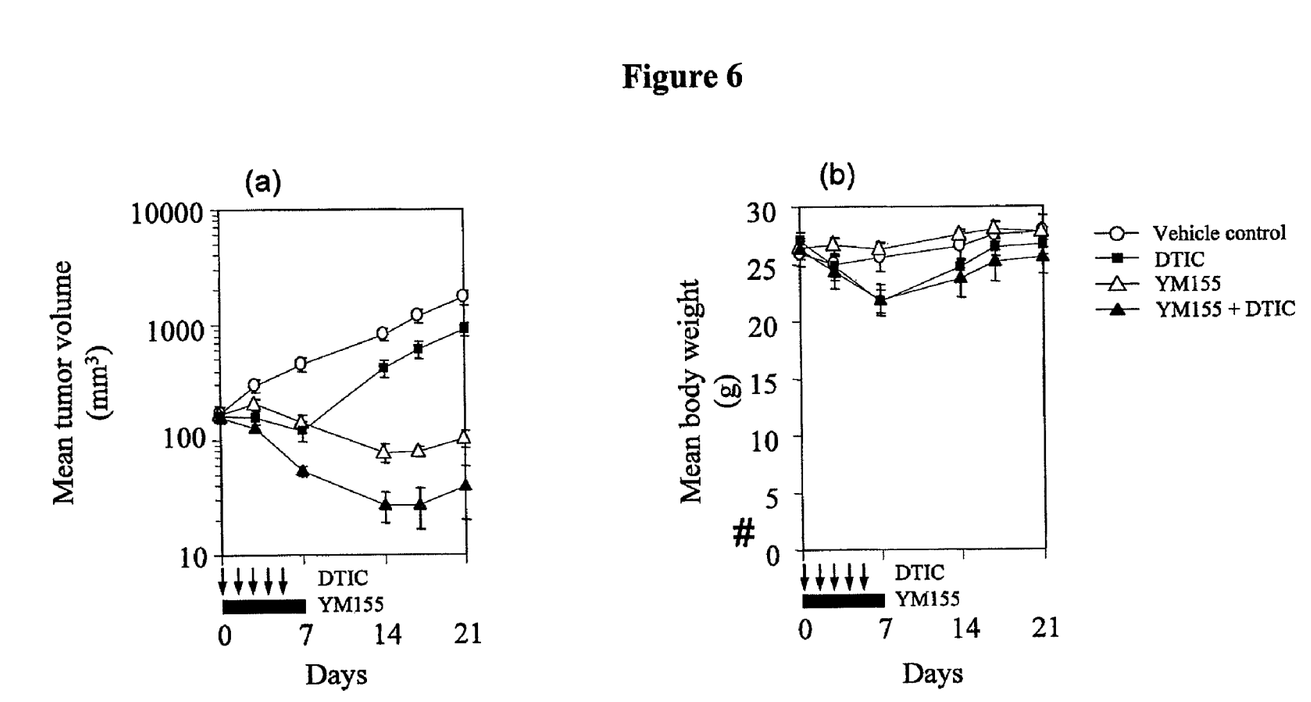
FIG. 6, (a) shows the mean tumor volume (mm³) from co-administration of YM155 and Dacarbazine (DTIC) in Test Example 4, and (b) shows the mean body weight (g), respectively.

The study was conducted in the same way as Test Example 1, except that Dacarbazine was used instead of Docetaxel and Melanoma A375 cells were used instead of Calu 6 cells according to the following dosage regimen (n=8). Results were shown in FIG. 6.

| | |
|---|---|
| YM155 group | YM155 3 mg/kg/day (7-day sc continuous infusion) |
| Dacarbazine group | Dacarbazine 200 mg/kg, 5 times weekly, i.v. |
| Combination group | YM155 3 mg/kg/day (7-day sc continuous infusion) + Dacarbazine 200 mg/kg, 5 times weekly, i.v. |

Dacarbazine was purchased as commercially available products, and prepared according to the procedure directed in package inserts to use in the tests.

Test Example 5

The study was conducted in the same way as Test Example 1, except that R-ICE(RICE) or Rituximab(RTX) was used instead of Docetaxel, and lymphoma WSU-DLCL-2 cells were used instead of Calu 6 cells according to the following dosage regimen.
YM155 group YM155 1 mg/kg/day (7-day sc continuous infusion)
RICE group RTX 50 mg/kg, i.v. (day 0)+(IFM 200 mg/kg+ETP 10 mg/kg), i.v. (day 1, 2 and 3)+CBDCA 30 mg/kg, i.v. (day 1)
YM155+RICE group YM155 1 mg/kg/day (7-day sc continuous infusion)+RTX 50 mg/kg, i.v. (day 0)+(IFM 200 mg/kg+ETP 10 mg/kg), i.v. (day 1, 2 and 3)+CBDCA 30 mg/kg, i.v (day 1).
YM155+RTX group YM155 1 mg/kg/day (7-day sc continuous infusion)+RTX 50 mg/kg, i.v. (day 0).

Figure 7:
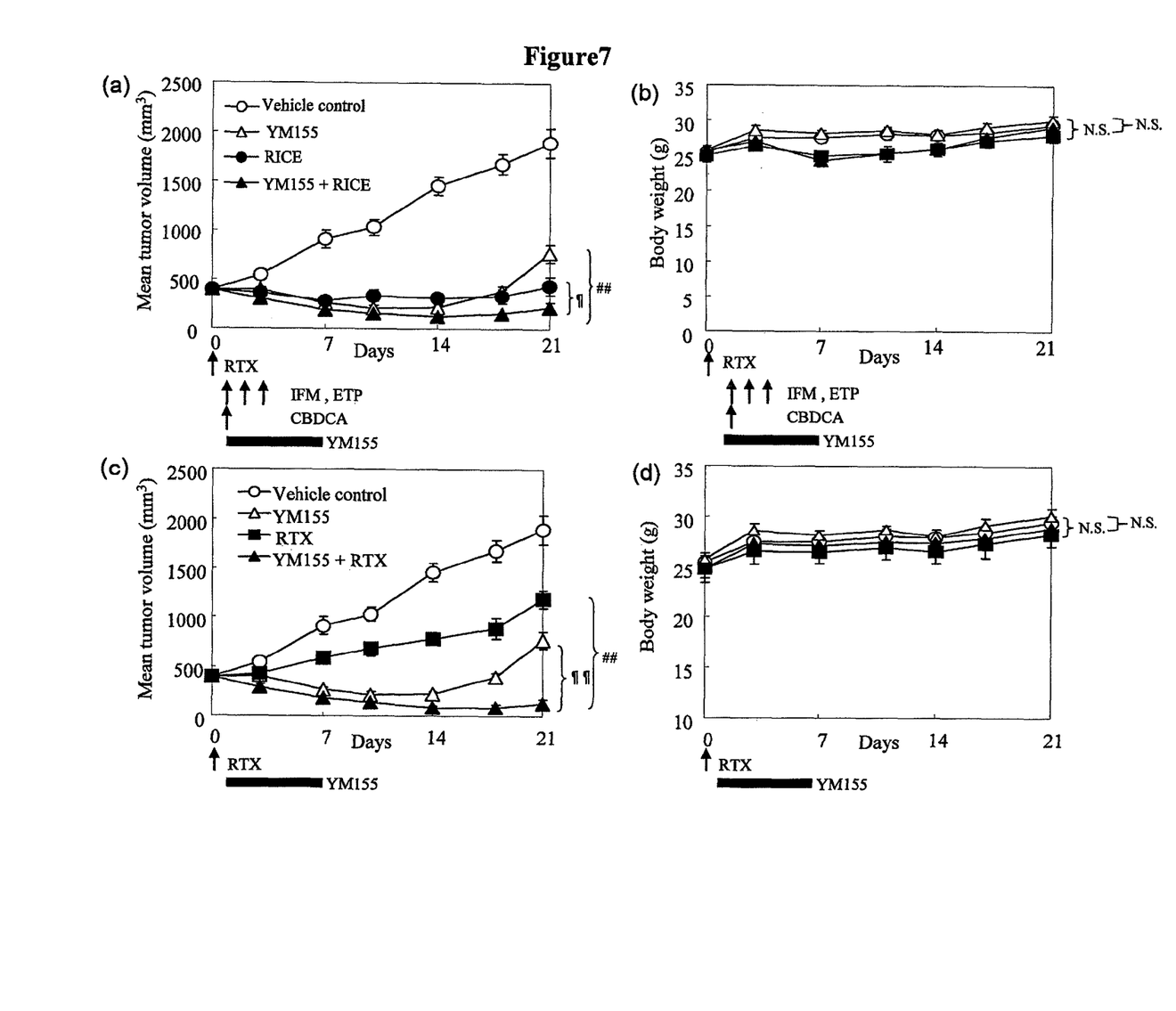
FIG. 7, (a) shows the mean tumor volume (mm³) from co-administration of YM155 and R-ICE (RICE) in Test Example 5, and (b) shows the mean body weight (g), respectively. And (c) shows the mean tumor volume (mm³) from co-administration of YM155 and Rituximab (RTX) in Test Example 5, and (d) shows the mean body weight (g), respectively.

RTX, IFM and ETP were purchased as commercially available products, and prepared according to the procedure directed in package inserts to use in the tests. Results were shown in FIG. 7. In the figures, values are expressed as the mean±SEM (n=6). ¶¶: P<0.01 versus an anticancer agent group, ¶: P<0.05 versus an anticancer agent group, ##: P<0.01 versus YM155 group, N.S.: no significance from YM155 group and the anticancer agent group (Student's t-test). YM155 in combination with R-ICE showed complete regression of the tumors in one case, and YM155 in combination with RTX showed complete regression of the tumors in two cases.

The preliminary study was done by using the method similar to the above-mentioned YM155+RICE group, but R-DHAP was used instead of R-ICE, wherein R-DHAP was consisting of rituximab (50 mg/kg i.v., day 0 and 2), cisplatin (5 mg/kg, i.v., day 2), cytarabin (70 mg/kg, i.v., day 4). The tumor volume was significantly (P<0.01) reduced in the combination group as compared to R-DHAP group on day 18.

Test Example 6

The study was conducted in the same way as Test Example 5 according to the following dosage regimen.
YM155 group YM155 2 mg/kg/day (7-day sc continuous infusion)
RICE group RTX 50 mg/kg, i.v. (day 6 and 8)+(IFM 400 mg/kg+CBDCA 30 mg/kg), i.v (day 9)+ETP 10 mg/kg, i.v (day 8, 9 and 10)
YM155→RICE group YM155 2 mg/kg/day (7-day sc continuous infusion)+RTX 50 mg/kg, i.v. (day 6 and 8)+(IFM 400 mg/kg+CBDCA 30 mg/kg), i.v. (day 9)+ETP 10 mg/kg, i.v. (day 8, 9 and 10)

Results were shown in table 6. In the table, values are expressed as the mean±SEM (n=8, RICE group: n=6). ¶¶: P<0.01 versus an RICE group, ##: P<0.01 versus YM155 group, N.S.: no significance from RICE group (Student's t-test). YM155 in combination with R-ICE showed complete regression of the tumors in six cases.

TABLE 6

| Treatment Groups | Tumor Volume (mm$^3$) | | Body Weight (g) | Antitumor Activity | Number of |
| | day 0 | day 28 | day 28 | (% inh/% reg) | CRs |
|---|---|---|---|---|---|
| Vehicle Control | 404.4 ± 14.5 | 2131.5 ± 276.6 | 29.02 ± 0.38 | — | 0/8 |
| YM155 | 405.1 ± 13.8 | 1181.3 ± 174.7 | 28.81 ± 0.23 | 45% | 0/8 |
| RICE | 404.2 ± 13.0 | 1356.0 ± 371.7 | 29.54 ± 0.51 | 56% | 0/6 |
| YM155 → RICE | 404.7 ± 12.6 | 17.6 ± 11.5$^{¶¶\#\#}$ | 28.55 ± 0.26$^{N.S.}$ | >100%/96% | 6/8 |

INDUSTRIAL APPLICABILITY

The method of the invention for treatment of cancer by co-administration of YM155 and an existing anticancer agent, in which the inhibitory action of YM155 on expression of survivin works synergistically with the anticancer effect of the existing anticancer agent, affords a high therapeutic effect for cancers and is useful in treatment of a variety of cancers to which existing anticancer agents are applied, accordingly. Thus, the method of the invention for treatment of cancer by co-administration of YM155 and an existing anticancer agent is useful in treatment of cancers, preferably all solid cancers and lymphomas, particularly skin cancer, bladder cancer, breast cancer, uterine cancer, ovary cancer, prostate cancer, lung cancer, colon cancer, pancreas cancer, renal cancer, gastric cancer, and the like. Particularly, they are expected as therapeutic agents for some kinds of cancers which show resistance against existing anticancer agents.

The invention claimed is:

1. A method for treatment of a cancer patient, which comprises administering an effective amount of 1-(2-methoxyethyl)-2-methyl-4,9-dioxo-3-(pyrazin-2-ylmethyl)-4,9-dihydro-1H-naphtho[2,3-d]imidazol-3-ium bromide to said patient, combined with
   i) rituximab,
   ii) a combination therapy R-ICE consisting of rituximab, ifosfamide, carboplatin and etoposide, or
   iii) a combination therapy R-DHAP consisting of rituximab, cytarabine and cisplatin as anticancer agents.

2. The method as claimed in claim 1, wherein rituximab is combined with said effective amount of 1-(2-methoxyethyl)-2-methyl-4,9-dioxo-3-(pyrazin-2-ylmethyl)-4,9-dihydro-1H-naphtho[2,3-d]imidazol-3-ium bromide.

3. The method as claimed in claim 1, wherein a combination therapy selected from the group consisting of R-ICE and R-DHAP is combined with said effective amount of 1-(2-methoxyethyl)-2-methyl-4,9-dioxo-3-(pyrazin-2-ylmethyl)-4,9-dihydro-1H-naphtho[2,3-d]imidazol-3-ium bromide.

4. The method as claimed in claim 3, wherein R-ICE is combined with said effective amount of 1-(2-methoxyethyl)-2-methyl-4,9-dioxo-3-(pyrazin-2-ylmethyl)-4,9-dihydro-1H-naphtho[2,3-d]imidazol-3-ium bromide.

5. The method as claimed in claim 1, wherein the patient has lymphoma.

6. The method as claimed in claim 1, wherein said 1-(2-methoxyethyl)-2-methyl-4,9-dioxo-3-(pyrazin-2-ylmethyl)-4,9-dihydro-1H-naphtho[2,3-d]imidazol-3-ium bromide is administered intravenously by infusion at a dose of 1-10 mg/m$^2$/day continuously for a period of 4-14 days.

7. A method as claimed in claim 6, wherein said 1-(2-methoxyethyl)-2-methyl-4,9-dioxo-3-(pyrazin-2-ylmethyl)-4,9-dihydro-1H-naphtho[2,3-d]imidazol-3-ium bromide is administered intravenously by infusion at a dose of 3-8 mg/m$^2$/day continuously for 7 days followed by 14 days of no 1-(2-methoxyethyl)-2-methyl-4,9-dioxo-3-(pyrazin-2-ylmethyl)-4,9-dihydro-1H-naphtho[2,3-d]imidazol-3-ium bromide, after which the entire administration cycle can be repeated depending on the patient's conditions.

8. A kit comprising at least one cycle dosage of 1-(2-methoxyethyl)-2-methyl-4,9-dioxo-3-(pyrazin-2-ylmethyl)-4,9-dihydro-1H-naphtho[2,3-d]imidazol-3-ium bromide and
   i) rituximab,
   ii) anticancer agents for a combination therapy R-ICE consisting of rituximab, ifosfamide, carboplatin and etoposide, or
   iii) anticancer agents for a combination therapy R-DHAP consisting of rituximab, cytarabine and cisplatin as anticancer agents.

* * * * *